United States Patent [19]
Wilkinson

[11] Patent Number: 5,413,111
[45] Date of Patent: May 9, 1995

[54] BEAD THERMISTOR AIRFLOW SENSOR ASSEMBLY

[75] Inventor: Mark A. Wilkinson, Marietta, Ga.

[73] Assignee: Healthdyne Technologies, Inc., Marietta, Ga.

[21] Appl. No.: 111,043

[22] Filed: Aug. 24, 1993

[51] Int. Cl.⁶ .............................................. A61B 5/087
[52] U.S. Cl. .................................... 128/724; 128/716; 128/736; 73/204.23; 73/204.26
[58] Field of Search ............... 128/716, 724, 736, 671; 73/204.23, 204.26; 338/22 R, 314; 374/163, 178, 185

[56] References Cited

U.S. PATENT DOCUMENTS

| | | | |
|---|---|---|---|
| 4,487,208 | 12/1984 | Kamens | 128/736 |
| 4,860,583 | 8/1989 | Olson | 73/204.15 |
| 5,161,541 | 11/1992 | Bowman et al. | 128/724 |
| 5,178,156 | 1/1993 | Takishima et al. | 128/724 |
| 5,190,048 | 3/1993 | Wilkinson | 128/724 |
| 5,251,636 | 10/1993 | Neuman | 128/724 |

FOREIGN PATENT DOCUMENTS 2575917  7/1986  France .................... 128/724

*Primary Examiner*—Krista M. Pfaffle
*Attorney, Agent, or Firm*—Foley & Lardner

[57] ABSTRACT

A bead thermistor air flow sensor assembly comprising bead thermistor and circuit conductor completely encapsulated between upper and lower layers of thin plastic film. The thermistors are mounted adjacent the outer ends of arms adapted to be aligned with the nostrils and mouth of the patient when the sensor assembly is positioned on the face of the patient by double faced mounting tape. The electrical circuit and bead thermistors being fully encapsulated and sealed, the assembly can be immersed in fluid for sterilization between uses. The assembly is thin and very flexible, permitting either face thereof to be applied to the patient to facilitate connection to monitoring equipment which may include an alarm to signal when normal breathing is interrupted.

9 Claims, 1 Drawing Sheet

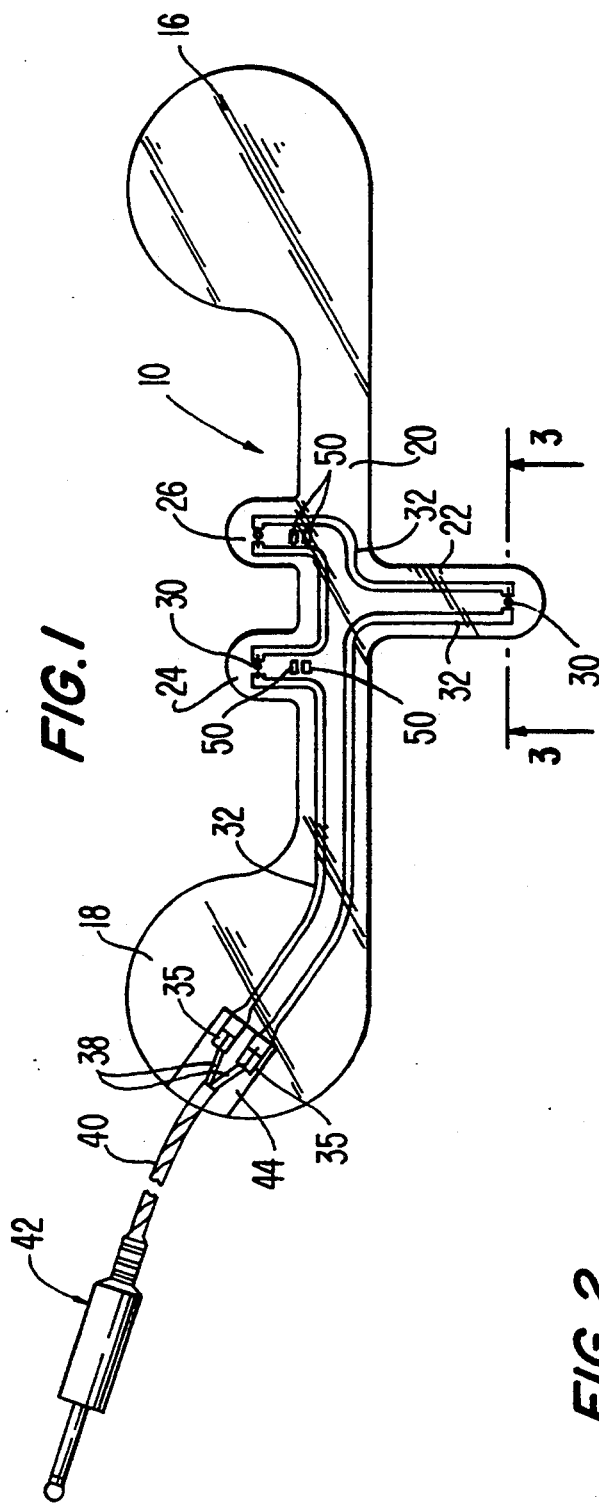
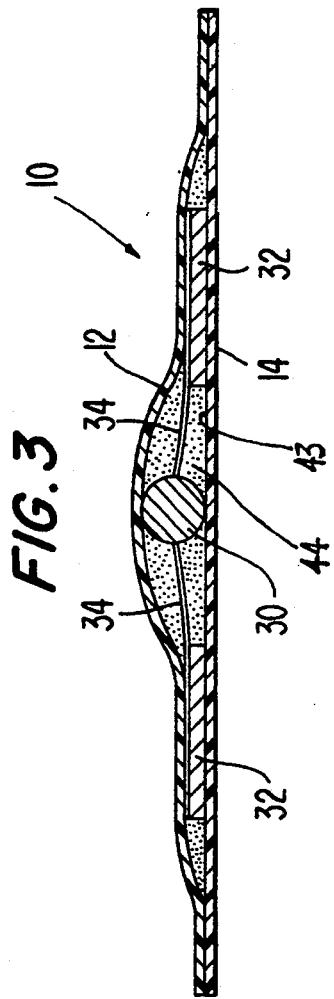
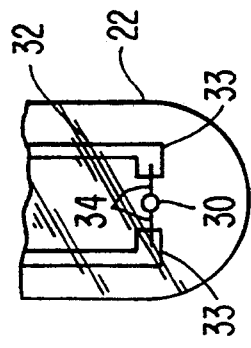

BEAD THERMISTOR AIRFLOW SENSOR ASSEMBLY

BACKGROUND OF THE INVENTION

The present invention relates, as indicated, to an airflow sensor assembly, and relates more particularly to a sensor assembly for monitoring the breathing of patients and in which a bead thermistor is employed to sense quickly and accurately differences between ambient temperature and the temperature of expired air, which temperature differences result in resistance changes in the thermistor.

The use of thermistors is widely known for diagnosing sleep apnea. In thermistor sensor systems, a thermistor is placed adjacent each nostril or naris of the nose and also adjacent the mouth so that nasal and oral airflow can be monitored. When breathing is normal, the monitoring circuit to which the thermistors are connected will pick up the resistance change in the thermistors due to the temperature differential between ambient and expired air, and provide a read out indicative of normal breathing. When there is at least a temporary cessation of expiration of air, this condition can be quickly picked up by the thermistors, with the sensor system typically providing both visual and audible alarms.

In the past, the use of thermistors in sensor assemblies has presented certain manufacturing and use problems. One proposed solution is disclosed in U.S. Pat. No. 5,190,048 of the present inventor. There is disclosed therein the use of chip thermistors mounted on a thin laminated film assembly. Although the sensor assembly employing the chip thermistors has proved satisfactory in use, there were certain attendant disadvantages both with respect to the manufacturing process and in the care of the assembly. Due to the dimensions and fragility of the chip thermistor, it was not possible to position the chip thermistor in sealed position between the top and bottom layers of film. As a result, it is necessary to laminate the film layers together so as to accommodate the location of each chip thermistor which protrudes exteriorly of the top layer of the assembly. Then, in order to electrically isolate the thermistors electrically and the adjacent conductors at each thermistor location, it is necessary to apply an inert thermally conductive conformal coating over the thermistors in order to seal the entire area.

The design disclosed in the '048 patent also had certain other disadvantages due to the size of the chip thermistor. In order to reduce the mass around the thermistor mounting, it was desirable to incorporate holes or openings in the laminated film on both sides of the long axis of the chip thermistor. This provides airflow around the thermistor so that it can respond better to temperature changes. In addition, the dimension in the area of each thermistor mount was such that it was possible to occlude the nares of infants and neonates. The use of thermistors of reduced size therefore became very desirable.

SUMMARY OF THE INVENTION

A primary object of the invention is to provide a bead thermistor airflow sensor assembly in which the bead thermistor can be secured to the lower film layer, and thereafter completely sealed and encapsulated by the outer film layer. This greatly facilitates the manufacturing process while at the same time providing an assembly that is faster and more sensitive to temperature change as well as one that is easier to clean. In accordance with the invention, bead thermistors 0.014" in diameter are used at each thermistor point and are applied to the bottom film layer prior to applying the top film layer. The bead thermistors are preferably welded to the flex circuit comprised of copper conductors, after which the top film layer is adhesively bonded to the bottom layer, fully enveloping, sealing, and isolating the bead thermistors. The bead thermistors are able to withstand the heat and pressure of the lamination process. This was not true with respect to the chip thermistors disclosed in the '048 patent.

A further object of the invention is to provide a sensor assembly which responds better to temperature changes. The glass bead thermistor is more sensitive than a chip thermistor and responds faster to temperature changes. Moreover, the dimensionally smaller bead thermistors permit sensor assemblies to be manufactured which are substantially smaller in size and particularly adapted to the facial dimensions of infants and neonates. The smaller bead thermistors permit smaller film areas around the mounting of the thermistors, which reduced mass allows the sensor assembly to respond more quickly to temperature change.

A further advantage of the invention is that by using the relatively small bead thermistors, the completed laminated assembly in which the bead thermistors are encapsulated is very low in profile and can be comfortably worn with either side of the assembly positioned toward the patient's face. This permits the cable extending from the sensor assembly to exit to either side of the bed depending upon the location of the monitoring equipment. In the sensor assembly disclosed in the '048 patent, the protrusion of the chip thermistors substantially beyond the upper film layer necessarily meant that as a practical matter, the sensor assembly could be positioned only in a single orientation.

These and other objects of the invention will be apparent to those skilled in the art as the following description proceeds in particular reference to the application drawings.

BRIEF DESCRIPTION OF THE DRAWINGS

FIG. 1 is a top plan view showing the sensor assembly of the present invention;

FIG. 2 is a fragmentary top plan view of a portion of FIG. 1, showing in more detail the connection of the copper conductors to the bead thermistor at one of the thermistor locations; and FIG. 3 is a sectional view taken on line 3—3 of FIG. 1, showing in greatly enlarged form and in more detail the mounting of the bead thermistor to the conductors and film layers.

DETAILED DESCRIPTION OF THE PREFERRED EMBODIMENTS

Referring to the application drawings, wherein like parts are indicated by like reference numerals, the sensor assembly of the present invention is generally indicated at 10. Upper and lower layers of film 12 and 14, respectively (FIG. 3), form the main body of the assembly, and can be secured at their interface by suitable bonding material, for example, an acrylic adhesive.

The body is configured to include enlarged pad portions 16 and 18 at opposite ends of the assembly, and a relatively narrow main body portion 20. A lower arm 22 and spaced upper arms 24 and 26, respectively, extend laterally from the main body portion 20, and bead thermistors commonly indicated at 30 are positioned near the end of each arm as will be described below in more detail when particular reference is made to FIGS. 2 and 3. The thermistors 30 are electrically connected to copper conductors commonly designated at 32. The thermistors are connected in series and the conductors 32 are preferably enlarged in the connecting area. As can be seen in FIG. 2, for example, the conductor 32 is enlarged as shown at 33 to provide a wider contact area for lead wires commonly indicated at 34 which are integrally formed with and extend from either side of the thermistor 30.

Contact pads 35 are provided for the connection of conductors 32 to lead lines commonly indicated at 38 of a cable 40 electrically connected to a plug generally indicated at 42. The plug preferably comprises an overmolded two conductor miniature phone plug that is commonly used in the field of airflow monitoring and is easily adaptable to various types of connections. The plug is completely sealed from moisture and the entire sensor assembly can be immersed for sterilization purposes.

The upper film layer 12 is spaced from the lower film layer 14 in the area immediately overlying the connection to the cable 40, with the spaced area being indicated at 44. The provision of the raised area reduces strain at the connection since the leads are soldered in place before the upper film layer 12 is adhesively secured to the lower film layer. However, the relief spacing is such that it does not prevent orienting the sensor assembly to the patient on either face of the sensor assembly.

The copper conductors are preferably provided on the top surface of the lower film layer 14 by etching. A common and preferred method of doing this is to first coat the entire surface of the lower film layer 14 with an acrylic adhesive 43 which can be sprayed or applied in sheet form. A layer of copper is then coated over the entire surface of the adhesive. The copper is then etched away in all areas except for those areas representing the conducting strips 32 and the wider contact areas 33. The thermistors 30 are placed on the lower film layer 14 after the etching process, and the lead wires 34 of the thermistors are secured at each connection preferably by arc welding, which is possible due to the exposed connections. Arc welding thereby eliminates the thickness of solder joints.

The arms 24 and 26 are adapted to be aligned with the nostrils of the user, and the lower arm 22 is adapted to be aligned with the mouth of the user. The use of bead thermistors allows for the width of each arm to be decreased to as low as 0.156" thereby adapting the assembly for infant and neonate patients.

The bead thermistors 30 are per se well known in the art, being manufactured by Thermometrics, Edison, N.J., and identified as Thermobead Series BR14. The bead comprises a glass bead thermistor approximately 0.014" in diameter, and as described the beads are applied to the lower film layer prior to lamination. The glass bead thermistors will withstand the heat and pressure required for laminating the upper and lower films together, which was not possible with the use of chip thermistors disclosed in U.S. Pat. No. 5,190,048.

The upper and lower film layers 12 and 14 are formed of very thin plastic film, for example, 0.002" in thickness. The polyamide film sold under the trademark "Kapton" by DuPont is preferred and has proved highly satisfactory in use. The films can be adhesively bonded in any suitable, well-known manner, for example, by an acrylic adhesive, with the total thickness of the assembly, excluding the relief area 44 and the region of the bead thermistors, being approximately 0.004" to 0.006".

During the copper etching process, lines of unconnected copper commonly designated at 50 are left in the arms 24 and 26. Each pair of adjacent lines 50 define therebetween a fold line which comprises an axis about which the outer ends of the arms 24 and 26 can be rotated or folded. The fold lines force the bending of the arms in the appropriate location. Accordingly, the arms are bent at an angle relative to the flat plane of the sensor assembly so as to be better exposed to normal airflow into and from the nostrils. When bent, the arms tend to remain in such bent position thereby providing for maximum flow of expired air over the thermistors.

The sensor assembly is manufactured as follows. The top surface of the bottom film layer 14 is coated with acrylic adhesive over its entire surface. A copper layer is then put down over the entire adhesive surface. The copper is then etched away to leave the copper conducting strips 32 and their widened ends 33, in addition to the lines 50. The contacts 38 of the lead wires are then welded to the conductor ends. The glass bead thermistors are then positioned as shown in FIGS. 2 and 3. To facilitate location, thermistor pads can be provided at such locations. The lead wires 34 of the bead thermistors are then welded to the adjoining enlarged copper portions 33 at each bead location. The circuit is now complete.

A further layer of acrylic adhesive 44, preferably in thin sheet form, is layered over the lower film and circuit and thermistor beads. The upper film 12 is then applied over the acrylic sheet. With the upper and lower layers of film properly aligned, the assembly is subjected to heat (approximately 500° F.) and pressure. As a result, the bead thermistors and related circuitry are fully encapsulated between the two layers which are firmly bonded throughout their contiguous surfaces. The adhesive is thermally activated and flows into and generally fills the area around the bead thermistors 30, as clearly shown in FIG. 3.

The resulting laminated sensor assembly is of very low profile, being essentially flat except for the regions around the bead thermistors and the relief area 44. Even in the areas of greatest thickness, either face of the assembly can be applied to the patient. This permits the plug 42 to extend to the side of the patient where the monitoring equipment is located.

As above noted, the relatively small bead thermistors permit the widths of the arms 22, 24 and 26 to be correlated for infant and neonate sizes, in addition to adult sizes of varying dimensions. In the smallest sizes, the size and spacing of the arms 22, 24 and 26, and the overall dimension of the assembly are such that the nostrils or nares of the infant are not occluded and the assembly can be effectively positioned on the face of the infant. Moreover, the relatively small bead thermistors permit the mass in the area of the thermistors to be reduced to the extent possible thereby allowing the thermistors to adapt to temperature changes more quickly. This is in addition to the fact that the smaller glass bead thermistors are inherently more sensitive than chip thermistors.

The sensor assembly 10 can be adhesively secured to the face of the user by any suitable double-faced mounting tape (not shown) which is per se well known in the art. The tape is preferably a foam tape with a double-sided adhesive layer and a release paper applied to each layer. A tape which has proved satisfactory in use is manufactured by the 3M Company under the product number 1511, with the tape comprising a double-sided, closed cell, hypo-allergenic PVC foam tape.

To use the thermistor tape referred to, the bottom release layer is removed and the tape is applied to the outer surface of either the film 12 or film 14. The foam tape is very similar in configuration and dimension to the sensor assembly, and extends at least over the pad portions 16 and 18 and the main body 20. After being adhered to the film 12 or 14, the other release paper is removed and the assembly applied to the face of the user, with the arms being aligned with the nostrils and mouth of the user, and the pad portions 16 and 18 extending to the cheek portions of the patient. The assembly can be mounted in place with only slight pressure, and can be maintained in place until removed. Because the sensor assembly is very thin, it is very flexible and can accommodate various facial curvatures. The entire assembly is very light in weight which further minimizes patient discomfort.

When in place, expired air passes over the chip thermistors 30, with the resistance of the thermistors varying accordingly and providing a signal which can be monitored in a well-known manner. If there is a cessation in breathing, the lack of temperature differential is picked up immediately. This signal can be recorded or used to activate audio and/or visual alarms.

The sensor assembly is normally applied at night when patients are most likely to be unattended. The assembly is normally removed the following morning when the patient is awake. At that time, the foam tape can be removed from the assembly, the assembly sterilized, and a new tape applied so that the assembly can be immediately reused. Since the foam tape is the only portion of the assembly which actually contacts the skin of the patient, the assembly can be repeatedly re-used with little or no deterioration. Since the bead thermistors and circuitry are entirely isolated and encapsulated, and the plug 42 completely sealed from moisture, the entire assembly can be immersed and sterilized in a suitable solution.

What is claimed is:

1. A thermistor airflow sensor assembly adapted to be mounted adjacent the mouth and nose of a patient for monitoring the breathing of such patient, comprising:
   (a) upper and lower layers of thin, flexible, resilient plastic film readily conformable to the facial curvatures of the patient, said layers being essentially identical in shape and configured to include an elongated main body strip, longitudinal end portions serving as primary mounting pads for the assembly, a first leg extending laterally from said main body strip and having an outer end adapted to be aligned generally with the mouth of the patient when the assembly is mounted, and a pair of longitudinally spaced second legs having outer ends and extending laterally from said main body strip in a direction opposed to said first leg, the outer end of each of said second legs being aligned with the nostrils of the patient when the assembly is mounted;
   (b) an electrical circuit comprising circuit conductors applied to said lower layer, said conductors extending to said outer ends of each of said legs and to a periphery of one of said end portions, and being adapted to be connected electrically to a monitor;
   (c) a bead thermistor for sensing air temperature mounted on said lower film layer adjacent the outer end of each of said first and second legs and electrically connected to said circuit conductors, said bead thermistors being located on said legs so that expired air from the patient's mouth and nose passes thereover;
   (d) said upper film layer fully enclosing and encapsulating said circuit conductors and said bead thermistors thereby electrically isolating said electrical circuit; and
   (e) adhesive bonding means for laminating said upper film layer to said lower film layer and encapsulating said bead thermistors and conductors, whereby said thermistor means detects the temperature change of ambient and expired air and transmits signals through said circuit indicative of such temperatures.

2. The sensor assembly of claim 1, wherein said circuit conductors comprise copper strips which extend generally diametrically through one of said longitudinal end portions, said sensor assembly further including a cable having connectors electrically connected to said copper strips, and wherein said upper film layer in the region of such connection is spaced from said lower layer film to form a strain relief area to minimize strain on the connection of said circuit to said cable.

3. The sensor assembly of claim 1, wherein each of said upper and lower layers of film comprise polyamide film approximately 0.002" in thickness, said layers being adhesively secured to each other thereby embedding said circuit conductors, the total thickness of said laminated assembly including said bead thermistors and said circuit conductors being approximately 0.006".

4. The sensor assembly of claim 1, further including a mounting tape adapted to be mounted on the exterior surface of either said upper or said lower film layers, said tape having a bottom release layer the removal of which permits the mounting tape to be secured adhesively to said layer, and a top release layer the removal of which permits the sensor assembly to be adhesively secured to the face of the patient, said mounting tape being configured similarly to each of said layers of film, whereby said mounting tape can be applied selectively to either of said layers whereby the assembly can be positioned on the face of a patient for more direct access to a monitor.

5. The sensor assembly of claim 1, wherein said first leg adapted to be aligned with the mouth of the patient is positioned generally centrally longitudinally of said upper and lower layers of film, and said second legs extending in a direction opposite to said first leg are positioned longitudinally to either side of said first leg, whereby said assembly is symmetrical when said second legs are aligned with the nostrils of the patient.

6. The sensor assembly of claim 5, wherein fold lines are provided in each of said second legs between said bead thermistors and the main body strip, each of said second legs being foldable about said fold lines to move said legs from a position coplanar with said main body strip to a position approaching perpendicularity with respect thereto, whereby said thermistors associated with each of said second legs is exposed more directly to the air expired through the nostrils of the patient.

7. The sensor assembly of claim 6, wherein said fold lines are provided by spaced strips of copper generally perpendicular to said circuit conductors, said spaced copper lines defining therebetween a pivot axis about which said legs can rotate relative to the plane of said main body strip.

8. The sensor assembly of claim 1, wherein said bead thermistors are 0.014″ in diameter, and wherein the width of each of said first and second legs is approximately 0.15″–0.16″ thereby permitting said assembly to be positioned on an infant or neonatal patient without said second legs occluding the nostrils of the patient.

9. The sensor assembly of claim 8, wherein the total thickness of the laminated assembly including said circuit conductors is approximately 0.006″.

* * * * *